(12) United States Patent
Peled et al.

(10) Patent No.: US 7,447,391 B2
(45) Date of Patent: Nov. 4, 2008

(54) PLANAR-RESONATOR BASED OPTICAL CHEMO- AND BIOSENSOR

(75) Inventors: Asher Peled, Even Yehuda (IL); Menachem Nathan, Tel Aviv (IL); Shlomo Ruschin, Herzlia (IL); Tali Zohar, Tel Aviv (IL)

(73) Assignee: Tel Aviv University Future Technology Ltd., Tel Aviv (IL)

( * ) Notice: Subject to any disclaimer, the term of this patent is extended or adjusted under 35 U.S.C. 154(b) by 0 days.

(21) Appl. No.: 11/568,570

(22) PCT Filed: May 5, 2005

(86) PCT No.: PCT/IL2005/000474

§ 371 (c)(1),
(2), (4) Date: Nov. 2, 2006

(87) PCT Pub. No.: WO2005/107368

PCT Pub. Date: Nov. 17, 2005

(65) Prior Publication Data

US 2007/0196043 A1     Aug. 23, 2007

Related U.S. Application Data

(60) Provisional application No. 60/569,635, filed on May 11, 2004.

(51) Int. Cl.
G02B 6/00 (2006.01)
G02B 6/12 (2006.01)
G02B 6/34 (2006.01)
G02B 6/10 (2006.01)

(52) U.S. Cl. .............. 385/12; 385/14; 385/37; 385/129; 385/143; 385/145

(58) Field of Classification Search ............ 385/12, 385/13
See application file for complete search history.

(56) References Cited

U.S. PATENT DOCUMENTS

| 2004/0078219 A1 | 4/2004 | Kaylor et al. |
| 2004/0223881 A1 | 11/2004 | Cunningham et al. |
| 2005/0135723 A1* | 6/2005 | Carr et al. ................... 385/12 |

OTHER PUBLICATIONS

T. Hirschfeld, J Callis and B. Kowalski Chemical Sensing in Process Analysis:, Science vol. 226 (1984) 312-318.
OS Wolfbeis, "Analytical Chemistry with Optical Sensors", Fresenius Z. Anal Chem, vol. 325 (9186) 387-392.

(Continued)

*Primary Examiner*—Michelle R. Connelly-Cushwa
(74) *Attorney, Agent, or Firm*—Mark M. Friedman (57) ABSTRACT

A biological or chemical optical sensing device comprises at least one planar micro-resonator structure included in a light emitting waveguide, and at least one biological or chemical probe bound to at least a part of the micro-resonator structure, the probe operative to bind specifically and selectively to a respective target substance, whereby the specific and selective binding results in a parameter change in light emitted from the waveguide. In one embodiment, the micro-resonator is linear. In some embodiments, the sensing device is active, the waveguide including at least one photoluminescent material operative to be remotely pumped by a remote optical source, and the parameter change, which may include a spectral change or a quality-factor change, may be remotely read by an optical reader.

33 Claims, 9 Drawing Sheets

OTHER PUBLICATIONS

J Scheuer et al, Proc . SPIE vol. 5333 (2004) pp. 183-194.
I Finkelstein et al Opt. Mater. vol. 7 (1997) p. 9.
Y.Xia and GM Whitesides, Ann . Rev.Mater.Science,vol. 28 (1998) pp. 153-184.
H. Zhang et al Nano Letters vol. 3 (1) pp. 43-45 2003.
S. Busse et al Sensors and Actuators B vol. 60 (1999) pp. 148-154.
J Dostalek et al Sensors and Acurators B vol. 76 (2001) pp. 8-12.
D. Hofstetter and RL Thoronton Proc SPIE vol. 3285 (1998) pp. 66-77.
W. Lukosz and K. Tiefenthaler, Sensors and Acuators vol. 15 pp. 273-284,1998.
I Szendro Proc SPIE vol. 4284 (2001) pp. 80-86 Abstract only.
Chan et al "Porous silicon microcavitis for biosensing applications"Phys Stat Sol.(a) vol. 182(2000) p. 541-546.
Chan et al "Nano microcavities for biomedical sensor applications" SPIE vol. 3912 (2000) p. 23-34.
Chan et al "Identification of gram negative becteria using nanoscale silicon microcavities" J.Am Chem. Soc. 2001, 123 11797-11798.
D. Windt "IMD- software for modeling the optical properties of multplayer films" Computes in Physics, vol. 12 N (1998) pp. 360-370.
J. Scheuer et al, Optics Letters, vol. 29 (Nov. 2004) pp. 2641-2643.
J. Scheuer and A. Yariv, Physical review E, vol. 70 (Sep. 2004) Paper No. 036603.
W. Koechner Solid—state Laser Engineering 4th ed p. 83 Springer 1996.
A. Yariv "optical Electronics in modern communications" Oxford University Press p. 492 (1997.

* cited by examiner

PLANAR-RESONATOR BASED OPTICAL CHEMO- AND BIOSENSOR

FIELD OF THE INVENTION

The present invention is related to the general field of optical sensors, and in particular to planar miniaturized electro-optical chemo- and biosensors comprising sol-gel photoluminescent resonant structures.

BACKGROUND OF THE INVENTION

Optical sensing devices that use effects based on the amplitude, phase, frequency, and state of polarization of electromagnetic radiation are known (see e.g. T. Hirschfeld, J. Callis and B Kowalski, "Chemical sensing in process analysis", Science, vol. 226 (1984) 312-318]. In chemo- and biosensors, all possible interactions between radiation and matter such as dispersion (refractive index), reflection (diffuse and specular), scattering (Raman), changing transmission, or quenching of fluorescence have been applied to monitor analyte/sensor interactions. Devices based on total internal reflection and evanescent-field effects are also known (see e.g. O. S. Wolfbeis, "Analytical chemistry with optical sensors", Fresenius Z Anal. Chem., vol. 325 (1986) 387-392). The aim of most development efforts in this field is toward achieving label-free, simple and cheap sensors with high sensitivity and specificity.

A sensitive layer comprising either a chemical or a biological ('receptor') material (also referred to as a "probe") is an essential part of chemo- and bio-sensor systems. As the difference between a chemical sensor and a biosensor lies mainly in the nature of this sensitive layer, the sensing principle being the same, we will refer henceforth to "biosensors" only, with the understanding that the present invention applies equally well to chemo-sensors. A good recent review of various types of optical biosensors and sensing principles may be found in U.S. patent application Ser. No. 20040078219 to Kaylor et al.

Label-free biosensors include in particular biosensors based on grating waveguides, some of which are sold commercially (see e.g. the OW 2400 sensor chip manufactured by MicroVacuum Ltd, Budapest, Hungary). These types of sensors couple a laser beam into the waveguide layer, and the in-coupling angle is very sensitive to the presence of absorbed molecules and to any change in the refractive index of the medium covering the chip surface. The amount of material absorbed on the grating can be determined sensitively from a precise measurement of the in-coupling angle ("angle interrogation"). Alternatively, the amount of material absorbed on the grating can be determined sensitively from a precise measurement of the in-coupling wavelength ("spectral interrogation"). A tunable light source is required in order to perform such a measurement, rendering it complex and expensive. Waveguide grating sensors are not known to be photoluminescent (PL) and therefore do not provide emitted light wavelength shifts for the detection of absorbed molecules.

Double grating sensors, which work on the angle interrogation principle are also known, see e.g. I. Szendro, Proc. SPIE vol. 4284 (2001) pp. 80-86. Label-free biosensors using an optical waveguide with induced Bragg grating of variable strength have also been suggested recentlyn (A V. Dotsenko et al. Sensors and Actuators B, vol. 94 (2003) pp. 116-121, 2003).

The application of resonant micro-cavity structures (also referred to herein simply as micro-cavities or micro-resonators) to optical biosensing is also known. Specifically, a biosensor based on a photo-luminescent porous silicon microcavity was disclosed by Chan et al. in various publications (Phys. Stat. Sol. (a) vol. 182, (2000) p. 541; Proc. SPIE, vol. 3912 (2000) p. 23; Comput. Phys. vol. 12, (1998) p. 360; J. Am. Chem. Soc. Vol. 123, (2001) p. 11797; and U.S. patent application Ser. No. 20020192680. Chan's device is a "bulk" device, which includes a porous semiconductor structure comprising a central layer interposed between upper and lower layers, each of the upper and lower layers including strata of alternating porosity; and one or more probes coupled to the porous semiconductor structure, the one or more probes binding to a target molecule, whereby a detectable change occurs in a refractive index of the biological sensor upon binding of the one or more probes to the target molecule. This type of sensor is therefore based on spectral interrogation using self-emitted light. A major problem with such a structure is that the sensed material has to diffuse into the sensor bulk (volume). Consequently, the sensor responds slowly, and the target material molecule size is limited to be much smaller than the pore size (which is typically in the 10 to 20 nm range). In addition, the emission of light from porous silicon is notoriously inefficient.

In a recent U.S. patent application Ser. No. 20040223881, Cunningham et al disclose an apparatus and method for detection of peak wavelength values of calorimetric resonant optical biosensors using tunable filters and tunable lasers. Biomolecular interactions may be detected on a biosensor by directing collimated light towards a surface of the biosensor. Molecular binding on the surface of the biosensor is indicated by a shift in the peak wavelength value of reflected or transmitted light from the biosensor, while an increase in the wavelength corresponds to an increase in molecular absorption. A tunable laser light source may generate the collimated light and a tunable filter may receive the reflected or transmitted light and pass the light to a photodiode sensor. The photodiode sensor then quantifies an amount of the light reflected or transmitted through the tunable filter as a function of the tuning voltage of the tunable filter. A major disadvantage of this scheme of detection is that the tunable filter transmits a different wavelength in each direction. Therefore, if the medium between the filter and the spectrometer is diffusive (like a biological cell extract or tissue) the measurement cannot be done. In addition, this setup is complex and expensive.

Also known are disk resonator photonic biosensors, see for example R W Boyd and J. E. Heebner, Applied Optics, vol. 40 (2001) pp. 5742-5747. These biosensors are based on high-finesse, whispering-gallery-mode disk resonators and operate by means of monitoring the change in transfer characteristics of the disk resonator when biological materials fall onto its active area. High sensitivity is achieved because the light wave interacts many times with each pathogen as a consequence of the resonant recirculation of light within the disk structure. Specificity of the detected substance can be achieved when a layer of antibodies or other binding material is deposited onto the active area of the resonator.

Further, radial Bragg ring resonators (also referred to as annular Bragg resonators or ABRs) are also known, as disclosed for example in U.S. patent application Ser. No. 20040247008 by J. Scheuer and A. Yariv, as well as in related publications (e.g. J. Scheuer et al. Proc. SPIE. vol. 5333 (2004) pp. 183-194; WMJ. Green et al. Applied Physics Letters vol. 85, (October, 2004) pp. 3669-3671; J. Scheuer et al., Optics Letters, vol. 29 (November, 2004) pp. 2641-2643; J. Scheuer and A. Yariv, Physical Review E, vol. 70, (September, 2004) paper No. 036603 Part 2; and W M J Green et al, J. Vac. Sci. Technol. B, vol. 22, (November/December, 2004) pp.

3206-3210). Such structures comprise a closed loop resonator having a distributed Bragg reflector for confining the light within a guiding core. In one embodiment, the light is confined from both the internal and the external sides of the device forming a guiding channel (defect), or just by the external side forming a disk resonator. Although the perfectly circular shape is generally preferred, the resonator could be of any closed loop shape such as an ellipse, etc. The Bragg reflectors can be of any type of distributed reflector such as, for example, a photonic bandgap crystal where the Bragg reflector is constructed by a series of holes in a dielectric material. The resonator may be used to obtain a laser. One limitation of such resonators is the requirement for a closed loop. Also, as reported in *Proc. SPIE.* vol. 5333 (2004), resonators fabricated in a 250 nm InGaAsP membrane had to be transferred and mounted on a sapphire substrate for better optical confinement of their modes, all rather complicated and expensive processes. There is also no enabling description of the use of ABRs for sensing prior to the priority date of this application.

There is thus a recognized need for, and it would be advantageous to have, a biosensor that can be spectrally interrogated from afar, and which is sensitive, has high specificity, and is inexpensive and simple to manufacture and use.

SUMMARY OF THE INVENTION

The present invention is of miniaturized electro-optical biosensing devices based on micro-resonant structures. A micro-resonator based sensor is also referred to hereinbelow as a "MRBS". In particular, one or more MRBS devices according to the present invention may be implemented in a sol-gel waveguide. More specifically, in a preferred embodiment, an "active" MRBS device according to the present invention comprises a planar electro-optical photo-luminescent micro-resonator comprising a central section and two bordering reflecting sections in the form of distributed Bragg reflectors (DBRs). In a preferred embodiment, the micro-resonator structure is linear. In other embodiments, it is non-linear, e.g. annular. A "passive" MRBS does not include a photo-luminescent material. In both cases, the structures involved are on micrometer and nanometer scales. Specific target-binding linkers (also referred to herein as receptors, linkers or "probes") may be embedded in these structures by means of biochemical and/or surface-chemistry processes. When embedded, the probes (e.g. antibodies, oligonucleotides, or other biological or chemical linkers) are an integral part of the device and serve as its "front end". A MRBS without probes may serve as a "dummy" in a differential measurement involving the dummy and a "real" sensor (with probes). The probes are embedded so that their specific association with a target material alters the optical properties of the entire device. The alteration is reflected in the modulation of light emitted from the device. The modulation may include an altered spectrum (for example, a shift of the emitted light wavelength or a change in the spectrum width, distribution or shape). The degree of modulation depends on the rate (amount) of target material association to the probes. Since the number of probes fixed to the device is constant, the emitted light alteration "reports" on the concentration of the target material. The optical readout is preferably performed at a distance from the micro-sensor. This principal characteristic, together with the small size and robust optical scheme of detection, make a sensor of the present invention ideal for use in both in-vitro and in-vivo applications.

In one embodiment, DBR corrugations of varying periods and with or without selective fixation of probes may be used to improve sensor properties such as sensitivity or dynamic range.

In another embodiment, surface plasmon resonance (SPR) elements may be embedded in the MRBS. The micro-resonator can be designed such as to have a sufficiently wide bandwidth. Conducting materials (such as gold or silver) can be embedded in the device to enable surface plasmon waves (SPWs) to be excited at certain wavelengths. Specific adsorption of the target material can alter the excitation spectrum of the SPW, thus altering the SPR dip(s) in the emitted spectrum In yet another embodiment, thin conducting patches (or stripes) may be embedded in the reflection corrugations to excite SPWs. This can improve the reflection corrugations response to target material binding, e.g. improve the field reflection coefficient alteration (amplitude and\or phase).

In yet another embodiment, the MRBS comprises certain sub-structures that uniquely and selectively bind the target material. These substructures are designed such that the quality factor (Q) of the whole micro-resonator is altered upon binding to the target material. This quality factor alteration mediated sensing, referred to hereinbelow as "QFAMS", can be used with both active and passive MRBSs. As further described below, in the active MRBS, the change in Q may be expressed (and measured) as a change of the emission spectral bandwidth (wavelength domain), or as a change in the emission relaxation time (time domain). In the passive MRBS, the change in Q may be expressed as a change in the MRBS spectral transfer matrix while using an external light source, or as a change in the relaxation time after excitation with an external light source.

According to the present invention there is provided a sensor comprising a substrate having a first refractive index and a planar waveguide formed on the substrate and having a second refractive index larger than the first refractive index, the waveguide comprising at least one micro-resonator structure on a waveguide surface opposite to the substrate, the micro-resonator structure operative to output a light signal that includes a spectral response to an interaction between a target substance and the micro-resonator.

Preferably, in the sensor, the micro-resonator includes a central section bound by two reflecting sections.

Preferably, in the sensor, each micro-resonator reflecting section includes a DBR.

Preferably, in the sensor, the waveguide is a sol-gel waveguide, and the sensor further comprises at least one probe selected from the group consisting of at least one biological target binding material and at least one chemical target binding material, the probe fixated to at least a part of the micro-resonator structure.

Preferably, in the sensor, the micro-resonator structure is linear.

Preferably, in the micro-resonator structure, the DBRs are identical.

Preferably, in the sensor, at least a part of the sol-gel waveguide includes at least one light emitting material that produces the light signal.

Preferably, in the sensor, the light emitting material includes a photoluminescent material.

Preferably, in the sensor, the sol-gel is selected from the group consisting of $SiO_2$, $TiO_2$ $SiO_2/TiO_2$, $Ta_2O_3$ and a mixture thereof.

Preferably, in the sensor, the DBRs include corrugations formed in the waveguide.

In some sensor embodiments, the waveguide is preferably a sol-gel waveguide and the micro-resonator structure is preferably linear and includes two reflecting sections bounding a central section, the reflecting sections including periodic perturbations formed on the waveguide, wherein the sensor further comprises at least one probe selected from the group consisting of at least one biological target binding material and at least one chemical target binding material, the probe fixated to at least a part of the micro-resonator structure.

In some sensor embodiments, the micro-resonator structure preferably includes sections at least partially covered by a thin layer of a material different from the sol-gel.

In some sensor embodiments, the material different from the sol-gel preferably includes at least one metal.

In some sensor embodiments, the at least one metal preferably includes gold.

In some sensor embodiments, the periodic perturbations are formed preferably on the waveguide using a soft lithography process.

In some sensor embodiments, the periodic perturbations preferably include a material selected from the group consisting of a probe and at least one metal.

According to the present invention there is provided a sensing device comprising at least one linear planar micro-resonator structure included in a light emitting waveguide, and at least one probe material bound to at least part of at least one micro-resonator structure, the probe material operative to bind specifically and selectively to a respective target substance, the specific and selective binding resulting in a parameter change in light emitted from the waveguide.

Preferably, in the sensing device, each linear planar micro-resonator structure includes a central region bound by two DBRs, the DBRs having corrugation tops and bottoms, the micro-resonator having at least one transverse mode.

Preferably, in the sensing device, the light emitting waveguide includes a sol-gel material doped with a photoluminescent (PL) material, whereby the sensing device is active.

Preferably, in the sensing device, the waveguide includes a sol-gel material, whereby the sensing device is passive.

Preferably, in the sensing device, the parameter change includes a measurable quality factor change.

Preferably, in the sensing device, the parameter change includes a measurable spectral change.

Preferably, in the sensing device, the spectral change includes a wavelength shift.

Alternatively, the sensing device further comprises at least one surface plasmon resonance (SPR) element coupled to the micro-resonator structure, wherein the parameter change includes a change in a resonant wavelength of the emitted light.

Preferably, the at least one transverse mode includes a plurality of N transverse modes, the device further comprising a plurality of longitudinal in-plane corrugations perpendicular to the DBR corrugations and operative to reduce the plurality to at least N−1.

According to the present invention there is provided, in various embodiments, optical sensing methods for sensing remotely an interaction between a probe and a target substance, comprising the steps of: providing one or more planar micro-resonators coupled to a light emitting waveguide, at least one of the micro-resonators having at least one probe bound to at least a micro-resonator surface part, promoting a specific and selective binding between the probe and the target substance, remotely pumping the waveguide, thereby causing a parameter change in light emitted from the waveguide though at least part of the micro-resonator, and remotely reading the parameter change.

Preferably, in some method embodiments, the step of providing at least one planar micro-resonator includes providing a linear planar micro-resonator.

Preferably, in some method embodiments, the step of reading the parameter change includes reading a spectral change.

Preferably, in some method embodiments, the step of reading a spectral change includes reading a wavelength shift.

Preferably, in some method embodiments, the step of reading a parameter change includes reading a quality-factor change.

Preferably, in some method embodiments, the step of reading a quality-factor change includes reading a change selected from the group consisting of an emission spectral bandwidth change and an emission relaxation time change.

Preferably, in some method embodiments, the step of providing at least one linear planar micro-resonator includes providing at least two micro-resonators, at least one micro-resonator having at least one probe bound to at least a micro-resonator part and at least another micro-resonator being probe-free, and wherein the step of remotely reading the parameter change includes reading the parameter change differentially.

An advantageous feature of the sensors of the present invention is that the energy consumed by the device is provided preferably by optical pumping of the PL material. The energy source may thus be remote from the device. In some embodiments, the sensor output is encoded by the wavelength distribution of the emitted light, and its readout is performed by remote spectral interrogation of this light. A variety of remote readers may be used, including spectrometers, monochromators plus detectors, or properly designed wavelength filters in conjunction with detectors. Because of the robust nature of spectral interrogation, in some constellations the remote readout may not require the extremely precise positioning typical of intensity-based measurements. In addition, the readout is not affected by changes in some system parameters, changes that are unavoidable in real use. The parameters may include distance between sensor and spectrometer, dirt or change of skin color\transparency (in in-vivo use), moisture, dust, or certain deviations of the reading system from the optimal position and direction. Spectral interrogation is also much less sensitive than angle interrogation to light scattering by a diffusive medium.

BRIEF DESCRIPTION OF THE DRAWINGS

The invention is herein described, by way of example only, with reference to the accompanying drawings, wherein:

FIG. 3 shows schematically perturbations that may be "built up" on top of the waveguide surface: (a) by exemplarily micro-stamping a thin receptor substance on the waveguide"; (b) by predefining (via e.g. lithography and/or a liftoff process) regions that are coated with a certain substance that binds probes exclusively;

FIG. 5 shows in: (a) a 3D image of an atomic force microscope (AFM) topography scan of a micro-resonator device fabricated in our laboratory; (b) a zoom of the nano-scale grating lattice; (c) a cross-section of the nano-scale grating lattice;

DETAILED DESCRIPTION OF THE PREFERRED EMBODIMENTS

Figure 1A:
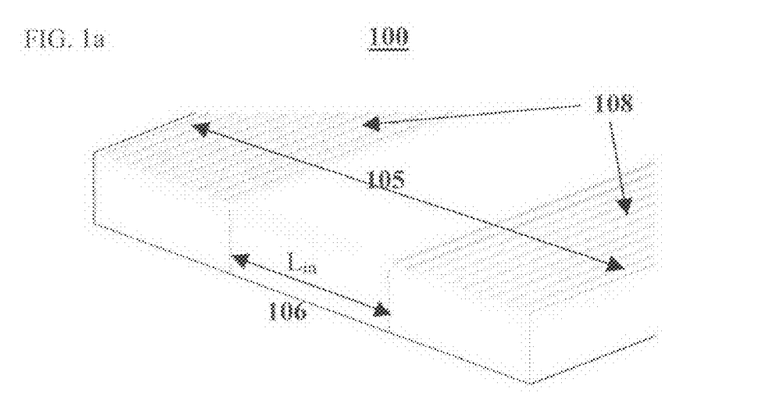
FIG. 1a-1d shows schematically a preferred embodiment of a linear waveguide-based MRBS according to the present invention.
Figure 1B:
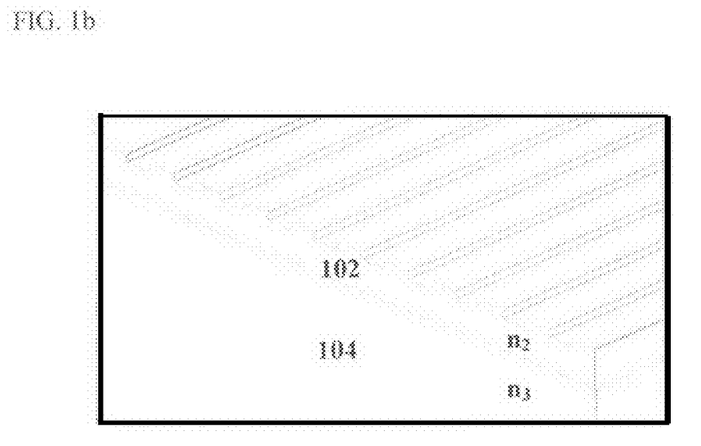
Figure 1C:
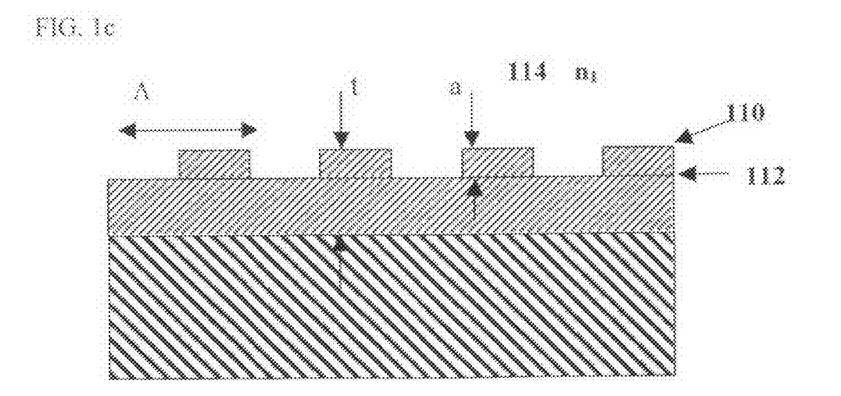

FIGS. 1a-c show schematically a preferred embodiment of a linear MRBS 100 according to the present invention. The MRBS includes a guiding layer (waveguide) 102 with a refractive index $n_2$ and thickness t formed on a substrate 104 with a smaller refractive index $n_3$. A planar micro-resonant structure 105 formed in waveguide 102 comprises a central section 106 with a length $L_{in}$ bound by reflection gratings or DBRs 108. The DBRs represent perturbations in the profile of layer 102 and are designed to support reflections of resonant electromagnetic modes, as explained in more detail in the model below. Each DBR has a corrugation structure with parameters defined by a period $\Lambda$ and a corrugation depth a that defines the distance between corrugation tops 110 and corrugation bottoms 112. The grating structure and the entire waveguide are faced on the side opposite to that of the substrate by a superstrate 114 medium with a refractive index $n_1$.

Waveguide layer 102 is made preferably of a sol-gel material including, but not limited to $SiO_2$, $TiO_2$, $SiO_2/TiO_2$, $Ta_2O_3$ and a mixture thereof. Alternatively, waveguide 102 may be made of other materials such as a polymer or a semiconductor material. When made of a sol-gel, layer 102 may be prepared using well-known sol-gel techniques (see detailed example below). In an "active" sensor embodiment according to the present invention, sol-gel layer 102 preferably incorporates a PL material such as Neodymium (Nd) or Erbium (Er) (possibly co-doped with Aluminum (Al) or other materials), or an organic die such as Rhodamine 6g, which is known to provide a very strong optical amplification (see e.g. I. Finkelstein et al, *Opt. Mater.* vol. 7 (1997), p. 9). The latter is important for providing a good overall signal-to-noise ratio. The PL material may be embedded in the entire resonator (including the waveguide body), exclusively in the non-corrugated central section 106, or exclusively in the DBR regions. Consequently, waveguide 102 includes a spread of PL sources that may be pumped optically, thereby obtaining spontaneous emission and/or stimulated emission whenever population inversion is reached.

Figure 5A:
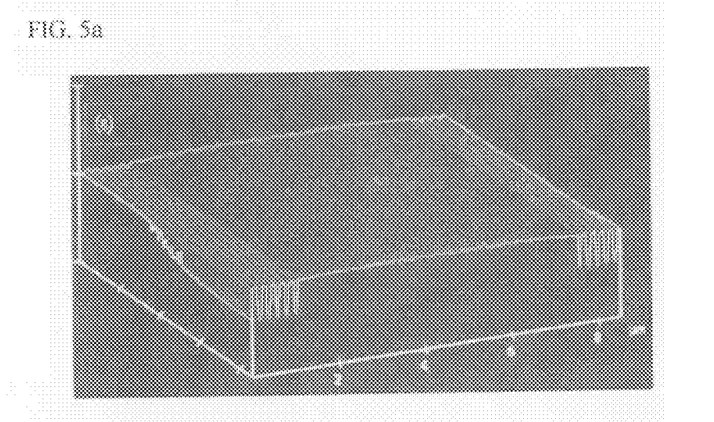

DBRs in sol-gel materials may be formed by various techniques: embossing as described for example in I. Szendro, *Proc. SPIE*, vol. 4284 (2001) pp. 80-86, other soft lithography techniques as described for example in Y. Xia and G. M. Whitesides, *Ann. Rev. Mater. Science*, vol. 28 (1998) pp. 153-184, or lithography and etching of the grating structure, as done in our laboratory and shown in FIG. 5.

Figure 1D:
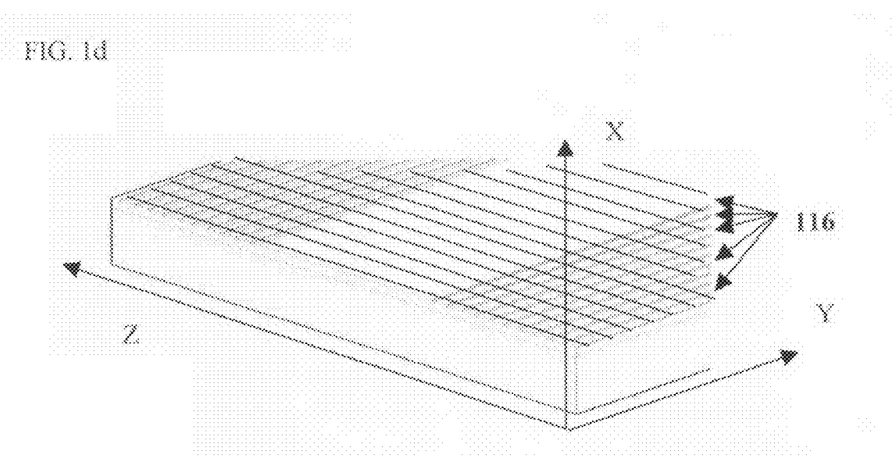

In order to reduce the number of transverse modes, (and under certain conditions, to achieve single transverse mode lasing operation) longitudinal corrugations 116 may be provided along the z axis, as shown in FIG. 1d. With reference to resonator parameters discussed in detail in the model below, the typical distance between corrugations 116 is on the order of a few to about 10 microns. The typical corrugation 116 slot width is on the order of a few hundred nanometers and up, and the typical corrugation depth is about a hundred nanometer and up. The addition of corrugations 116 slightly changes the propagation constant $\beta$ (see model below) relative to that of a classical planar waveguide. The change can be easily calculated, using for example the well-known effective index method. Alternatively, high transverse modes can be avoided by increasing the DBRs diffraction losses, e.g. by using narrow DBRs to border a large $L_{in}$.

Figure 2:
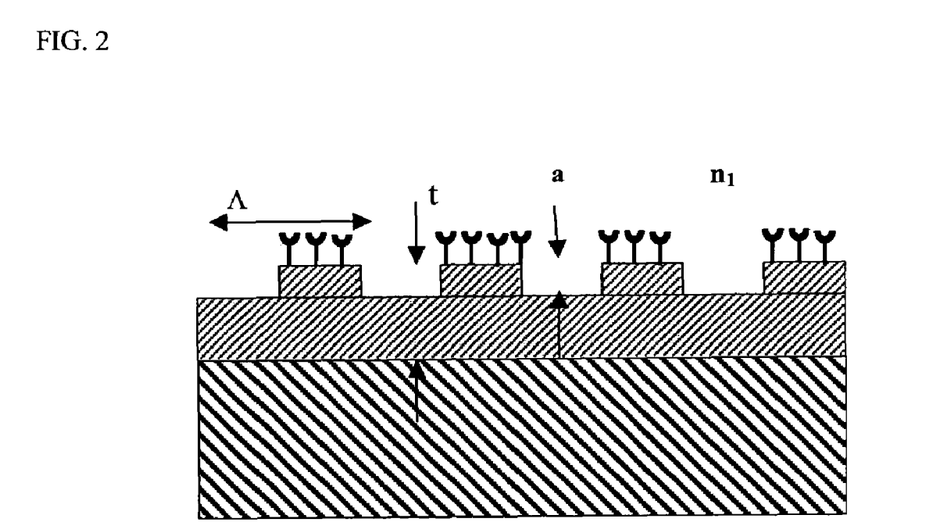
FIG. 2 shows a selective DBR top receptor binding scheme.

Probes (bio-receptors or chemical linkers) may be bound to the sensor over the entire resonant structure ("whole resonator binding") or only in the DBR sections ("selective binding"). Binding to the DBRs may include binding to all DBR corrugation surfaces (i.e. both tops and bottoms), referred to below as "full DBR binding"; selectively to either the DBR corrugation tops or bottoms ("selective DBR top binding" and "selective DBR bottom binding" respectively); or further selectively to only some of the corrugation tops or bottoms ("selective partial DBR binding"), e.g. to every second DBR period or top or bottom. FIG. 2 shows such a selective DBR top binding scheme.

Specific adsorption of target-material molecules to probes on structure 105 and/or central section 106 and/or DBRs 108 can change the propagation constant $\beta$ as a function of the optical frequency (e.g. via interaction with the evanescent field). This leads to alterations in the spectral properties of the resonance. The resonance wavelength and the linewidth can be shaped by proper design of the waveguide profile and of the perturbation parameters of the DBRs. This allows optimization of the MRBS sensitivity to target-material adsorption.

Figure 3A:
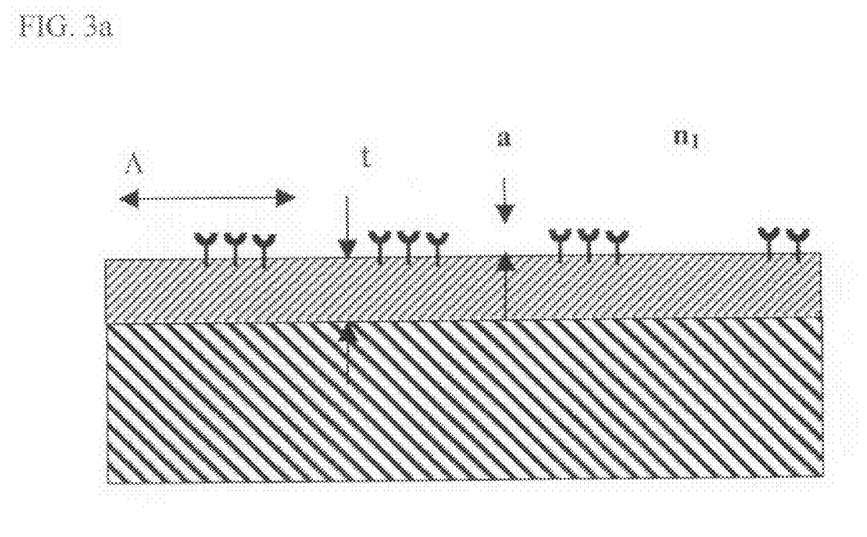
Figure 3B:
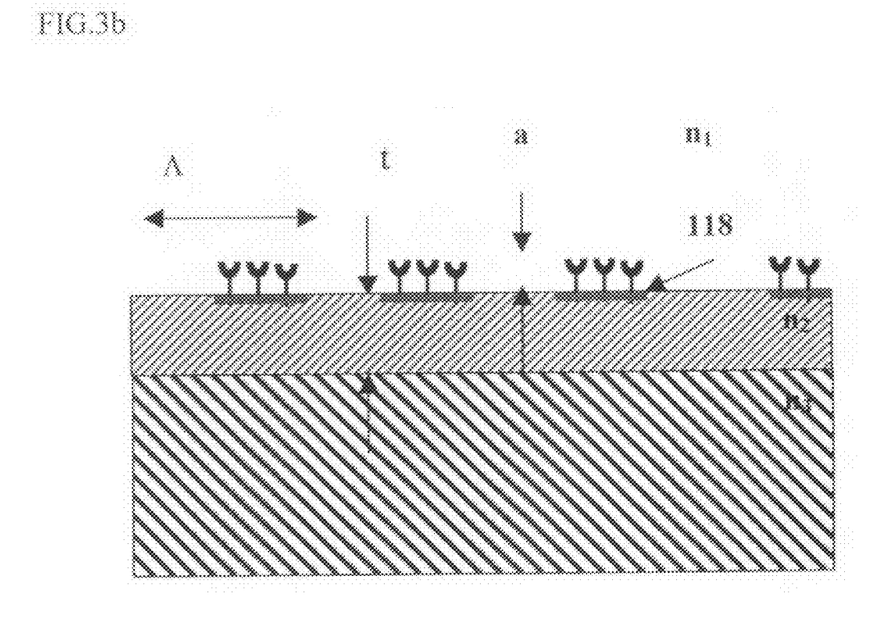

Alternatively, as shown in FIGS. 3a-b, corrugation-type perturbations may be formed directly on a flat waveguide surface: (a) using either the probes themselves (e.g. by microstamping) or (b) receptors bound to an additional layer 118 (e.g. a linker or metal). These "built-up" corrugation type perturbations are designed to support reflections, i.e. act as DBRs. In FIG. 3(b), the linker or metal (e.g. gold) layer may be first deposited on the waveguide uniformly to a required thickness, then patterned and etched to yield a corrugation pattern (also referred to as metal stripes). A suitable process is described for example in H. Zhang et al. *Nano Letters* Vol. 3 (1), pp. 43-45, 2003. Alternatively yet, gold stripes may be formed using a lift-off technique. Alternatively, a gold layer may be formed on existing (pre-formed) DBR corrugation tops or bottoms. It would be evident to one skilled in the art that such thin gold stripes may be formed selectively on all tops, all bottoms, both tops and bottoms or only selected tops and/or bottoms of pre-formed DBR corrugations. Furthermore, the metal layer may comprise more than one metal, for example first chromium and on top gold. The metal layer may be made extremely thin (nanometer size) to have a small impact on the electromagnetic wave propagation in the waveguide. The gold stripes may be used to directly bind bio-molecules, e.g. through the well-known chemistry of thiol-gold bonding, as described for example in S. Busse et al, in *Sensors and Actuators B*, vol. 60 (1999) p. 148-154. These gold stripes may be therefore used to define specific regions on the sensor surface to which probes are then bound exclusively. Materials other than gold may also be used with a suitable chemistry.

The exclusive target material binding to the probes provides an effect similar to adding a layer with an effective refractive index of the target material. In the selective DBR top binding case, this enlarges the effective depth of the corrugation and therefore enhances the DBR reflectivity. In the selective DBR bottom binding case, this reduces the corrugation effective depth and hence reduces the DBR reflectivity. These effects are shown in detail in the model below.

Figure 4A:
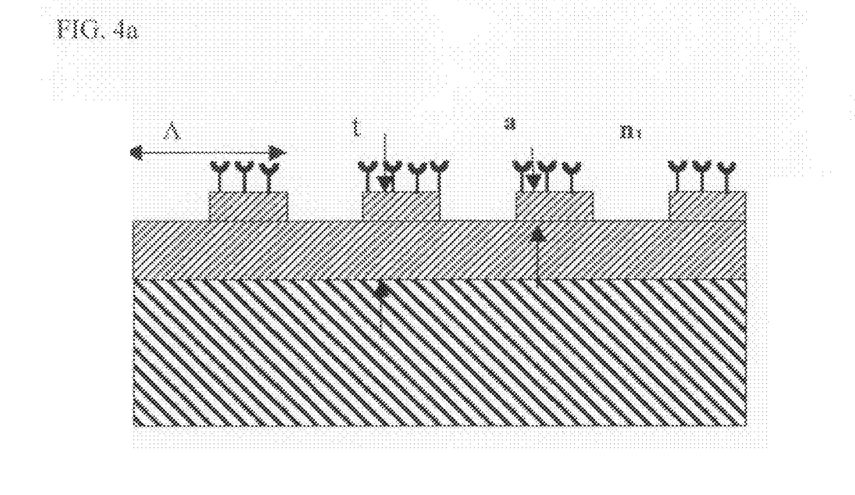
FIG. 4a shows exemplarily a grating structure obtained by a combined micro-embossing and micro-stamping process.

FIG. 4a shows exemplarily a grating structure that may be obtained by a combined micro-embossing and micro-stamping process. The DBR is first formed using a first material on the waveguide layer, and subsequently only alternating DBR sites (corrugation tops 110) are stamped with a bio-receptor or linker, yielding a DBR structure with alternating binding sites. This alternate binding scheme is expected to further increase the sensitivity of the MRBS, as explained in the QFAMS mechanism. Yet, alternatively, the corrugation teeth could be built on the waveguide surface using a first material (e.g. by stamping) followed by another stamping process that binds probes on top of the teeth.

Figure 4B:
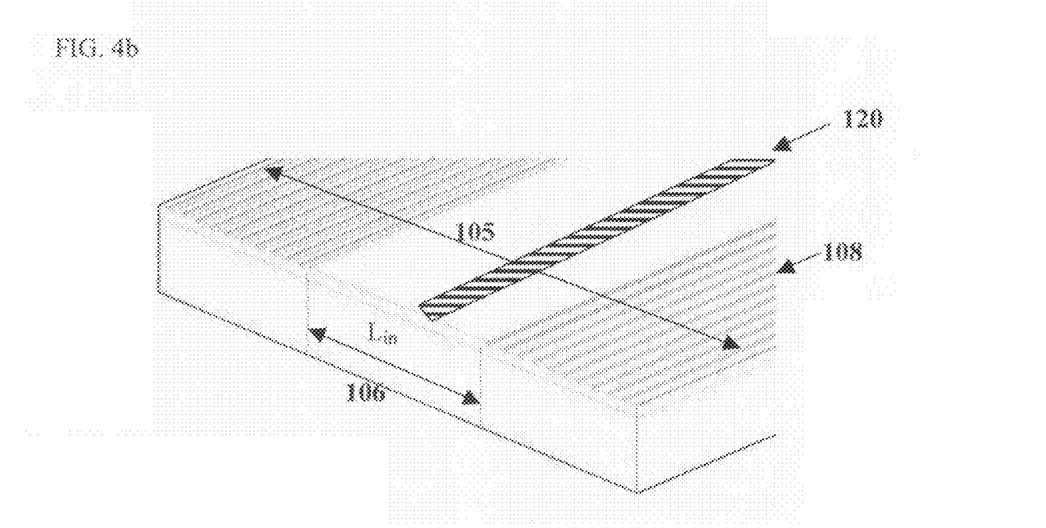
FIG. 4b shows an embodiment of a micro-resonator configured for SPR/SPW sensing.

FIG. 4b shows an embodiment of a micro-resonator configured for SPR/SPW sensing. The sensor comprises at least one SPR element 120 in the form of a thin metal stripe coupled to the central section of the micro-resonator, in parallel with the DBR corrugations. The SPR element provides an additional mechanism for sensing. The addition of an SPR element to a section of a waveguide structure changes the propagation constant of the guided light if any modification takes place on the upper surface of the metal stripe (J. Dostalek et. al. *Sensors and Actuators B*, vol. 76 (2001) pp. 8-12). The change in the propagation constant translates both into a change of the resonant wavelength emitted by the structure and of its line-width.

In the embodiments in FIGS. 2, 3 and 4a, the change in the DBR reflectivity leads to change in the Q of the entire resonator, as explained below. Sensing mediated by a quality factor alteration, i.e. QFAMS, can be applied both to active and passive MRBSs. The QFAMS can be performed using a number of different methods as explained below with reference to equations 17 and 20-22. In the active MRBS, the change in the Q may be expressed (and measured) as a change of the emission spectral bandwidth (frequency domain) see e.g. W. Koechner, *Solid-State Laser Engineering*, 4$^{th}$. Ed. p. 83 Springer, 1966, or by a change in the relaxation time of the emission (time domain) see e.g. D. Hofstetter and R. L. Thornton *Proc. SPIE*, vol. 3285 (1998) pp. 66-77. In the passive MRBS, the change in the Q may be expressed as a change in the spectrum of either the transmission or reflection coefficients while using an external light source, or as a change in the photon relaxation time after excitation with an external light source.

Further, the binding schemes shown in FIGS. 2, 3 and 4a may be used to alter (upon binding of target material) the effective depth of penetration of the electromagnetic waves into the DBR structure, and hence the effective length of the resonator. The higher transverse mode diffraction losses at the DBR reflections are consequently changed, altering the resonator oscillation conditions for these modes. A well-known estimation for the amount of transverse (lateral) modes in a resonator is given by the Fresnel number $$d^2/\lambda L \tag{1}$$

where d is the resonator width (in our case approximately the DBR width), $\lambda$ is the wavelength and L is the resonator length. The alteration is reflected in the reduction of the number of oscillating transverse modes per each longitudinal mode order. In the cases where the transverse peaks of each longitudinal order are spectrally attached, the aforementioned phenomenon leads to a change in the spectral bandwidth of each longitudinal resonant peak. The two latter effects can be used as the sensor readout.

Figure 5B:
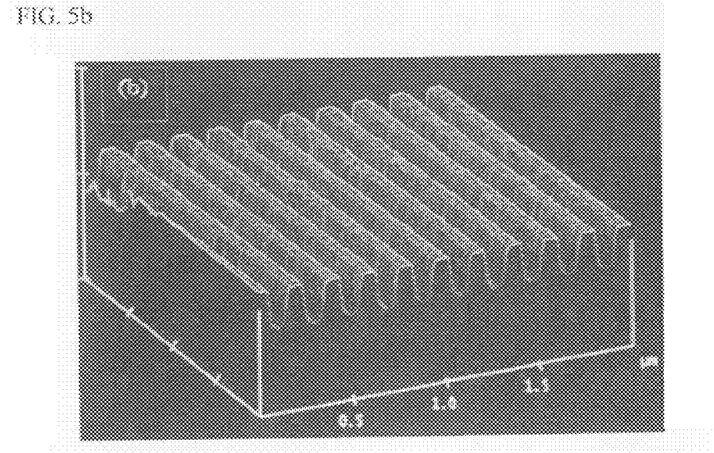
Figure 5C:
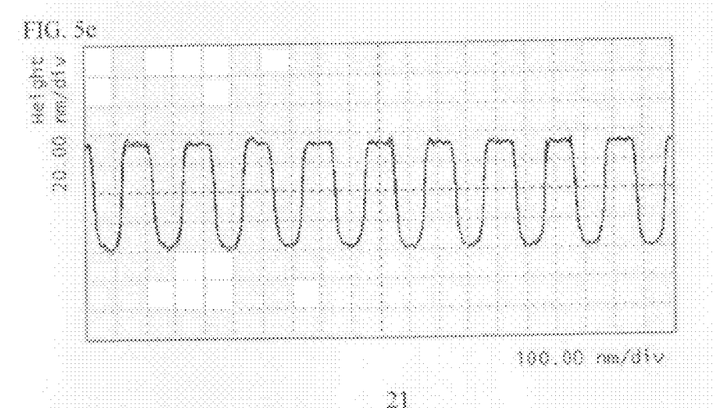

FIG. 5a shows a 3D image of an atomic force microscope (AFM) topography scan of a micro-resonator device comprising a central section bordered by two nano-scale grating lattices (DBRs). The device was fabricated in our laboratory in a sol-gel waveguide containing Rhodamine 6G laser dye, using PMMA mediated electron-beam lithography followed by a reactive ion etch. FIG. 5(b) shows details of the DBR corrugations and FIG. 5(c) shows an AFM profile of the DBR corrugations.

The spectral interrogation sensing principle of a preferred embodiment of an active MRBS of the present invention is further explained with the assistance of the following model.

Physical Model, Mathematical Formulation and Computer Simulation

As mentioned, in the active MRBS embodiments (e.g. of FIG. 1), energy transfer occurs by means of external optical pumping of the PL material in the waveguide. By solving the wave equation in each media and by demanding continuity of the proper field components, we end up with the eigenvalue equation (the TE case is represented, TM being similar):

$$tg(h_m t) = \frac{p_m + q_m}{h_m(1 - p_m q_m / h_m^2)}; \tag{2}$$

where the solution field function is $$E_{y_m} = E_{y_m}(x) e^{-i\beta_m z + i\omega t'}; \tag{3}$$

$\beta_m$ being the propagation constant of mode m, and $h_m$, $q_m$, $p_m$ defined as follows:

$$h_m = \sqrt{n_2^2 k_0^2 - \beta_m^2}\,; \tag{4}$$

$$q_m = \sqrt{\beta_m^2 - n_1^2 k_0^2}\,;$$

$$p_m = \sqrt{\beta_m^2 - n_3^2 k_0^2}\,;$$

$k_0 = 2\pi/\lambda_0 = \omega/c_0$, $c_0$ is the vacuum speed of light, $\omega$ is the optical frequency, t' denotes the time dependence, t is the guiding layer thickness, and the $E_y(x)$ function is:

$$E_{y_m}(x) = \begin{cases} c_m e^{-q_m x} & 0 \leq x \leq \infty \\ c_m(\cos(h_m x) - q_m/h_m \sin(h_m x)) & -t \leq x \leq 0 \\ c_m(\cos(h_m t) - q_m/h_m \sin(h_m t))e^{p_m(x+t)} & -\infty \leq x \leq -t \end{cases} \tag{5}$$

where $c_m$ is the $m^{th}$ mode normalization coefficient given by $$c_m = 2h_m \sqrt{\frac{\omega\mu}{|\beta_m|(t+1/q_m+1/p_m)(h_m^2+q_m^2)}} \quad (6)$$

We refer to the corrugations as to periodic perturbations in the refractive index as a function of x and z, and we Taylor-expand the functional z dependence $$\Delta n^2(x,z) = \Delta n(x) \sum_{q=-\infty}^{\infty} a_q e^{i(2q\pi/\Lambda)z}. \quad (7)$$

Using the perturbation theory of coupled modes (A. Yariv, "Optical Electronics in Modern Communications", Oxford University Press, 1997), we obtain the coupling between the backward propagating $m^{th}$ mode and the forward propagating $m^{th}$ mode (the amplitudes of which are designated by $A_m^-$ and $A_m^+$ respectively):

$$\frac{dA_m^-}{dz} = A_m^+ \underbrace{\frac{i\omega\varepsilon_0}{4}\int_{-\infty}^{\infty}\Delta n^2(x)E_y^2(x)dx\, a_l}_{\kappa_{m-m}\equiv\_coupling\ coefficient} e^{(2l\pi/\Lambda-2\beta_m)z} \quad (8)$$

where l is the expansion order for which the phase-matching condition is fulfilled:

$$2l\pi/\Lambda - 2\beta_m \approx 0 \quad (9)$$

Terms not expressly defines here may be found in the Yariv reference (e.g. on p. 492). The rest of the expansion terms that do not comply with the phase-matching condition can be neglected, because their contribution will induce and reduce the amplitude in an oscillating manner, so that their coupling contribution averages to zero. Their deviation changes are small, because of the relatively short distance at which they go out of synchronization. For corrugations, the z function of the index perturbation is a periodic step function. Therefore $$a_q = \begin{cases} -i/\pi q & q \in \text{odd} \\ 0 & q \in \text{even} \\ 1/2 & q = 0 \end{cases} \quad (10)$$

and $$\Delta n^2(x) = \begin{cases} n_1^2 - n_2^2 & -a \le x \le 0 \\ 0 & \text{elsewhere} \end{cases}. \quad (11)$$

If we choose to design for the first order (q=1), $$\kappa_{m-m} = \frac{\omega\varepsilon_0}{4\pi}\int_{-\infty}^{\infty}\Delta n^2(x)E_{y_m}^2(x)dx \quad (12)$$

$$= \frac{\omega\varepsilon_0}{4\pi}(n_1^2 - n_2^2)\int_{-a}^{0} c_m^2(\cos(h_m x) - q_m/h_m \sin(h_m x))^2 dx$$

The same treatment holds for energy coupling from the backward propagating mode to the forward one. Hence, we basically have a set of the two coupled-mode equations:

$$dA_m^-/dz = \kappa_{m-m}A_m^+ e^{-i2\Delta\beta z} \text{ and } dA_m^+/dz = \kappa_{m-m}^* A_m^- e^{+i2\Delta\beta z} \quad (13)$$

where we define:

$$\Delta\beta_m = \beta_m - \pi/\Lambda. \quad (14)$$

For a total corrugation grating length of L starting at z=0, to which a modal wave is entering with an amplitude $A_m^+(0)$, the solution to the set of the coupled mode equation is:

$$A_m^-(z)e^{i\beta_m z} = A_m^+(0)\frac{i\kappa_{m-m}e^{i\beta_0 z}}{-\Delta\beta_m\sinh(sL)+is\cosh(sL)}\sinh(s(z-L)) \quad (15)$$

and $$A_m^+(z)e^{-i\beta_m z} = A_m^+(0)\frac{e^{-i\beta_0 z}}{-\Delta\beta_m\sinh(sL)+is\cosh(sL)} \quad (16)$$

$$\{\Delta\beta_m\sinh(s(z-L)) + is\cosh(s(z-L))\}$$

where $$S \equiv \sqrt{|\kappa_{m-m}|^2 - (\Delta\beta_m)^2}.$$

Hence, the reflection coefficient term is:

$$\rho_m(\lambda) = \frac{A_m^-(0)}{A_m^+(0)} \quad (17)$$

$$= \frac{-i\kappa_{m-m}\sinh(\sqrt{|\kappa_{m-m}|^2-(\Delta\beta_m)^2}\,L)}{-\Delta\beta_m\sinh(\sqrt{|\kappa_{m-m}|^2-(\Delta\beta_m)^2}\,L) + i\sqrt{|\kappa_{m-m}|^2-(\Delta\beta_m)^2}\cosh(\sqrt{|\kappa_{m-m}|^2-(\Delta\beta_m)^2}\,L)}$$

The total field is therefore a self-interference of the spontaneous/stimulated emission spatial spectral component with its infinite series of echoes. If we denote by $\rho_1, \tau_1$ and $\rho_2, \tau_2$ the reflection and transmission coefficients of DBR1 and DBR2 respectively, and by $L_{in}$ the inner resonator length between DBRs, we can formulate the mathematical expression of the total field at the outer surface of DBR2:

$$E_{out}(\omega) = E_s(\omega)e^{-i\omega t}\tau_2(\omega)e^{i\beta(L_{in}-z)}\left[\frac{1+\rho_1(\omega)e^{i\beta 2z}}{1-\rho_1(\omega)\rho_2(\omega)e^{i\beta 2L_{in}}}\right] \quad (18)$$

where z is the position of the emitting PL source (the z-axis origin is located at the inner surface of DBR1). For the cases of only spontaneous emission, in order to include all the spontaneous emission contributions of the PL sources spread in the device, we integrate at the power level assuming absolute incoherence between the different sources.

$$|E_{tot}(\omega)|^2 = |E_s(\omega)|^2|\tau_2(\omega)|^2 \begin{bmatrix} 1+|\rho_1(\omega)|^2 + \\ \frac{i}{2\beta}\left(\begin{array}{c}\rho_1(\omega)(1-e^{i\beta 2L_{in}})+ \\ \rho_1^*(\omega)(e^{-i\beta 2L_{in}}-1)\end{array}\right) \\ 1+|\rho_1(\omega)\rho_2(\omega)|^2 - \\ 2\,\text{Real}\,(\rho_1(\omega)\rho_2(\omega)e^{i\beta 2L_{in}}) \end{bmatrix} \quad (19)$$

Spectral_transfer_function_of_the_microresonator

A Matlab code was written in order to carry out the aforementioned calculations. Given the waveguide's parameters, the code numerically finds the propagation coefficients β (and the effective index) as a function of λ for a large number of wavelengths in order to produce well-refined spectral calculations of the waveguide resonator. The code accepts the desired central wavelength of operation $\lambda_0$ as a parameter. Its respective propagation coefficient $\beta_0$ is then calculated, and consequently the corrugation period Λ is found by the requirement for phase matching $\beta_0 = \pi/\Lambda$. Finally the field reflection coefficient and the resonator spectral transfer function are numerically calculated as a function of wavelength. These calculations are done in a particular manner at all of the sample wavelengths within the span. At each wavelength computation point, the coupling coefficient $\kappa_{m^-m}$ is recalculated for this specific wavelength, for the sake of accuracy.

The Matlab code was used to run a simulation of the whole sensor action. Assumed refraction indexes were 1.333 (water solution) for the superstrate, 1.75 for the sol-gel waveguide, and 1.47 (Pyrex glass) for the substrate. The effective index of the guided mode is denoted $n_{eff}$ and the adsorption layer thickness is denoted $d_{ad}$. It has been shown that maximum sensitivities $(\partial n_{eff}/\partial d_{ad})_{max}$ are achieved with a guiding-layer thickness of 1.5-2 times the cut-off thickness [see W. Lukosz and K. Tiefenthaler, *Sensors and Actuators*, vol. 15, pp. 273-284, 1998]. In that regime, adsorption of a protein layer with a refractive index of approximately 1.45 causes an effective index change of $\Delta n_{eff} \sim 2.5*10^{-4}$ per each nm of the adsorbed layer. Hence, for a 4 nm-thick adsorbed layer, $\Delta n_{eff} \sim 10^{-3}$. Accordingly, a waveguide thickness of 200 nm was used in the simulation. The design of the other parameters of the micro-resonator is governed by the spectral interrogation considerations: exemplarily, we designed for a micro-resonator line width of the order of 0.5 nm. The corrugation depth was designed to be 0.2 of the total waveguide thickness (i.e. a/t=0.2), the micro-resonator length between the gratings was 6.01 micron, and the number of grating periods was 50.

Figure 6:
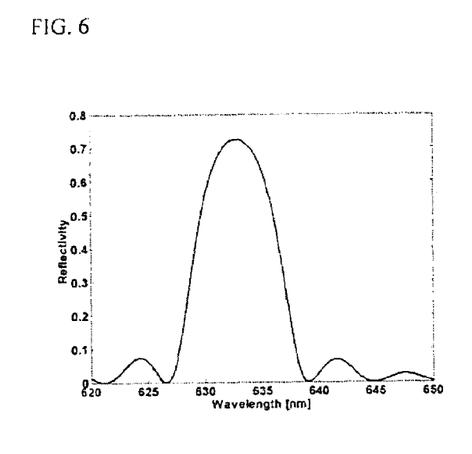
FIG. 6 shows the power reflection coefficient of a simulated grating with a full width at half maximum (FWHM) of 8 nm.
Figure 7:
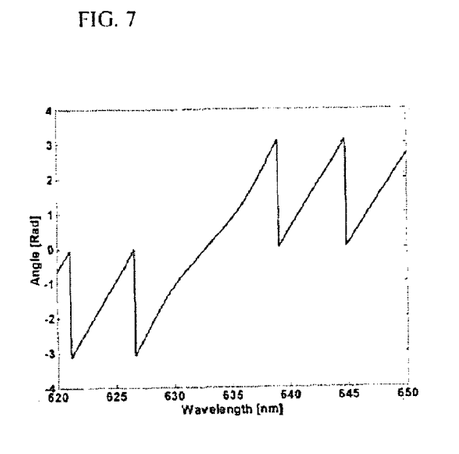
FIG. 7 shows the phase of the field reflection coefficient of the simulated grating of FIG. 6.
Figure 8:
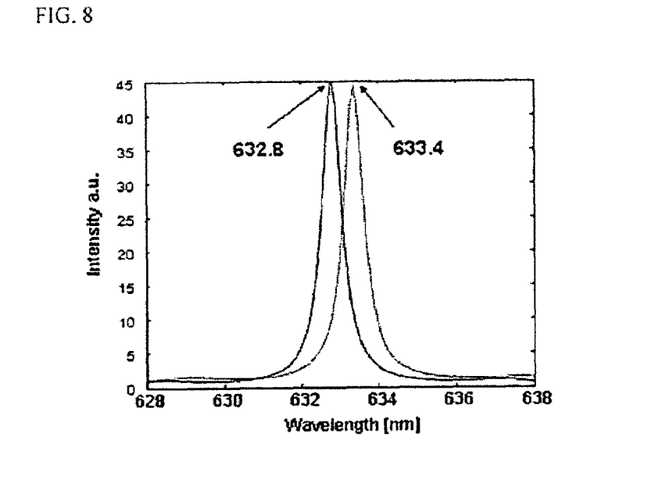
FIG. 8 shows the emission spectrum of a micro-resonator designed for a working wavelength of 632.8 nm, before and after the simulated adsorption of a 4 nm thick protein layer, which causes a change of $10^{-3}$ in the mode effective index.

FIG. 6 shows the power reflection coefficient of this grating, and FIG. 7 shows the phase of the field reflection coefficient. The power reflection coefficient has a full width at half maximum (FWHM) of 8 nm. FIG. 8 shows the emission spectrum of the entire micro-resonator, which was designed for a working wavelength of 632.8 nm. As seen, the FWHM is 0.6 nm. FIG. 8 also shows the emission spectrum (at 633.4 nm) of the micro-resonator, after the adsorption of a 4 nm thick protein layer. The 0.6 nm spectral shift in the resonance peak can be measured accurately, e.g. by a spectrum analyzer.

Using the field reflection coefficient as a function of the corrugation parameters and geometry, equation (17), the power reflection coefficient $R=\rho_m^2$ can be used to evaluate the resonator quality factor Q;

$$Q = 2\pi[1 - \exp(-T_0/\tau_c)]^{-1} \approx \frac{2\pi\tau_c}{T_0} = \omega_0\tau_c \qquad (20)$$

where the photon cavity lifetime $\tau_c$ is given by:

$$\tau_c = \frac{2ln_{eff}}{c}[\ln(R_1R_2)^{-1} + 2\alpha l]^{-1} \qquad (21)$$

for threshold operation. l is the cavity length, α represents overall losses in the resonator, $\omega_0$ is the optical angular frequency $T_0$ is the corresponding time period and $R_1$, $R_2$ are the power reflection coefficients of the DBRs. Under other operation conditions the functional dependence of $\tau_c$ with respect to the power reflection coefficients can be somewhat different.

Figure 9A:
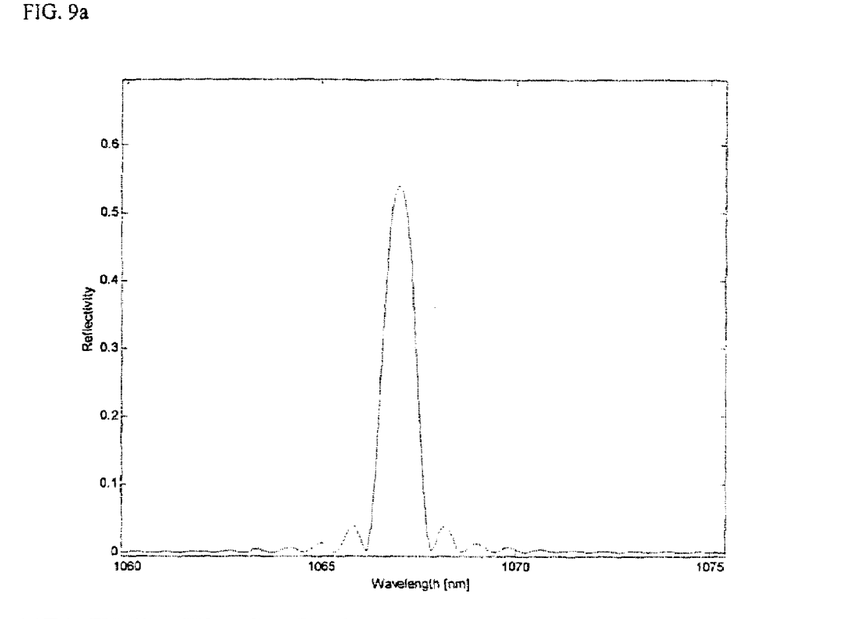
FIG. 9a-9b shows the change of the power reflection coefficient R responsive to binding of a 4 nm-thick protein layer.
Figure 9B:
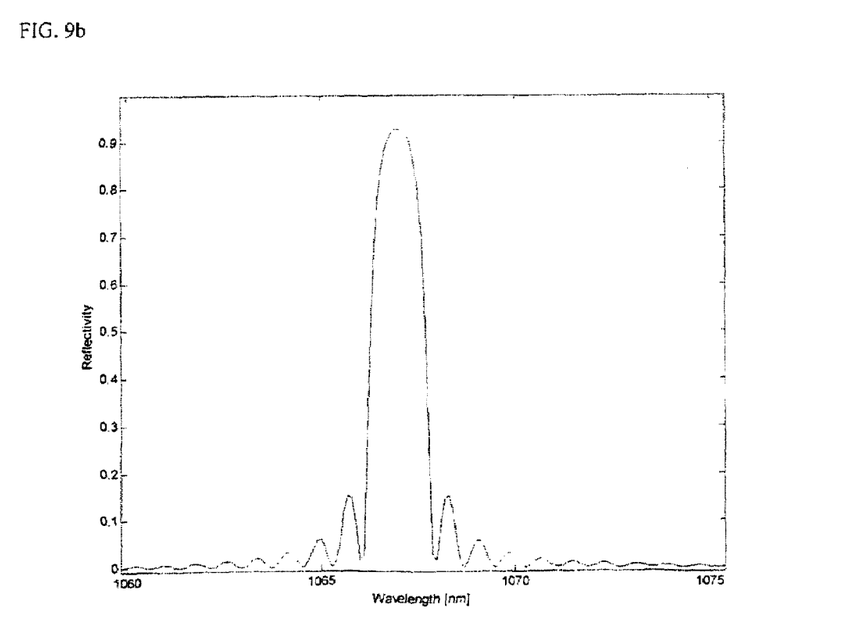

FIG. 9 shows the change of R in response to binding of a 4 nm-thick protein layer to a 200 nm-thick waveguide with substrate index $n_3$=1.44 (fused silica), guiding layer index $n_2$=1.81 (sol-gel) and superstrate index $n_1$=1.33 (water). The DBR has 600 periods and the corrugation depth is 3 nm. It can be seen that R changes dramatically from a value of 0.54 before the binding, FIG. 9(a), to a value of 0.925 after the binding FIG. 9(b). This changes in turn the Q-factor of the entire resonator, as explained in equations (20) and (21) above. The Q is also related to the resonator bandwidth;

$$Q \approx 2\pi\omega_0/\Delta\omega_0 \qquad (22)$$

where $\Delta\omega_0$ is the optical bandwidth. The change in the Q-factor can be used for sensing with both active and passive MRBSs, using the methods referred to above.

SENSOR FABRICATION EXAMPLE

Sol-Gel-Waveguide Fabrication Process

Titania-silica waveguides used in the present invention were fabricated using the sol-gel technique. The sol-gel process is based on inorganic polymerization formed by hydrolysis and condensation reactions of organometallic compounds in alcoholic environment. The most studied system is polymerization of silicon-alkoxides.

nSi(OR)$_4$+4nH$_2$O→nSi(OH)$_4$+4nROH Hydrolysis nSi(OR)$_4$→Si$_n$O$_{2n}$+2nH$_2$O Condensation In a preferred embodiment, the precursors are ethanol, acetic acid, titanium ethoxide, and GLYMO (3-GLYcidoxypropyl)triMethOxysilane). Such a reaction system is described for example in Y. Sorek et al. *Appl. Phys. Lett.* 63 (24) 1993. The precursor solution is refluxed for 2-4 hours, while the following reactions take place:

Ti(OEt)$_4$+CH$_3$COOH→CH$_3$COOTi(OEt)$_3$+EtOH

CH$_3$COOH+C$_2$H$_5$OH→CH$_3$COOC$_2$H$_5$+H$_2$O

Ti(OEt)$_4$+4H$_2$O→Ti(OH)$_4$+4EtOH

R—Si(OCH)$_3$+3H$_2$O→R—Si(OH)$_3$+3CH$_3$O

A PL material (e.g. Rhodamine 6G dye or Nd$_2$O$_3$ co-doped with Al$_2$O$_3$) is added to this chemical reaction system and the solution is then filtered and cooled. The product solution, ready for spin coating and curing, can be stored for weeks without degrading the quality of the layer.

The waveguide was designed to be of high index and thin, allowing its power-filling factor to be reduced, while still supporting a guided mode. Under these conditions, the evanescent field in the superstrate carries a larger part of the optical power of the mode. Therefore, it enhances the sensitivity of the mode propagation coefficient to index changes in the superstrate, particularly to the adsorption of a layer of biomolecules (or other target material). Sol-gel waveguides fabricated in our laboratory had a high refractive index of 1.83 as measured by an ellipsometer.

Figure 10:
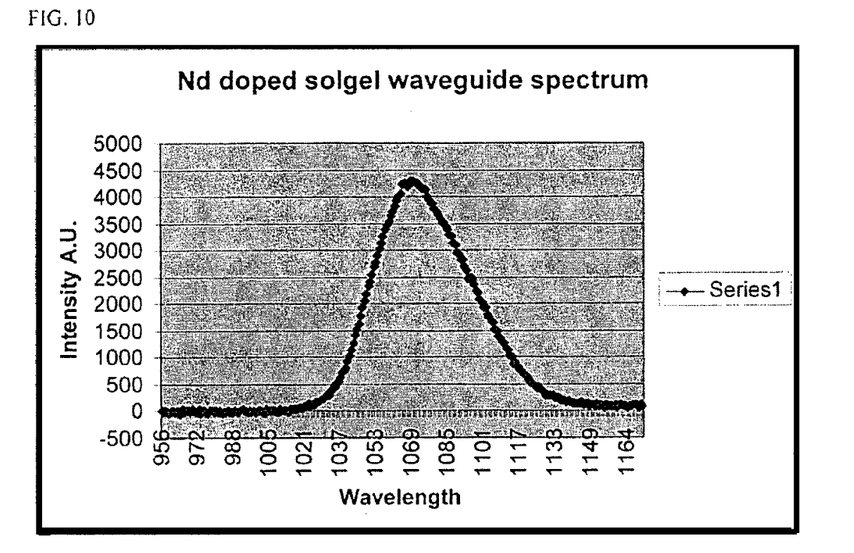
FIG. 10 shows a measured photoluminescent spectrum of a sol-gel waveguide fabricated in our laboratory.

FIG. 10 shows a measured PL spectrum of a sol-gel waveguide fabricated according to the process detailed above. The waveguide was doped with 1% Nd+3 ions and co-doped with 10% Al+3 ions, and optically pumped with a 810 nm laser diode.

Fixation of Bio-Receptors to the Device

Figure 11:
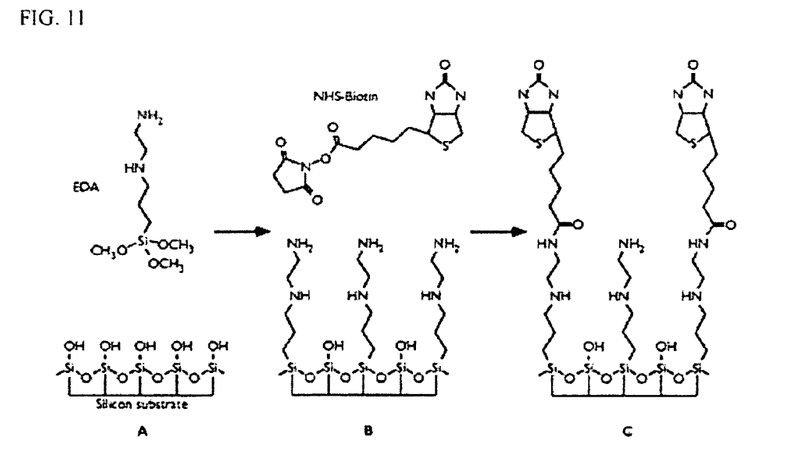
FIG. 11 shows an exemplary procedure for biotinylating the silica surface of the sensor.

FIG. 11 shows an exemplary procedure for biotinylating the silica surface of the sensor. A typical procedure included forming N-2-aminoethyl-3-aminopropyltrimethoxysilane (ADE) films on the silica surface by immersion in an acidic solution of 1% silane for 30 min at room temp. The surfaces were subsequently rinsed and heated to 120° for 3 min to obtain covalent condensation of the silanes. The silane films were immersed in 1 mM Biotin-N-hydroxysuccinimide ester (NHS-biotin) in dry DMSO. The NHS-biotin was then reacted with the primary amine of the ADE.

In summary, the present invention discloses planar micro-resonator sensors fabricated in a planar sol-gel waveguide. In some embodiments, the sol-gel may be doped with a PL material. In our sensors, the target material is absorbed on the sensor surface, in contrast with micro-resonant bulk sensors as disclosed by Chan, in which the target material has to diffuse into the bulk of the sensor through long and narrow (10 nm) nano-channels. Therefore the response of our sensors is rapid, and there is absolutely no limitation regarding the target material molecules sizes.

While the invention has been described with respect to a limited number of embodiments, it will be appreciated that many variations, modifications and other applications of the invention may be made. In particular, one skilled in the art would appreciate that more than one micro-resonator may be formed on a substrate with waveguide. One or more reference dummy micro-resonators identical with a MRBS but lacking the receptor (probe) layer may be used in conjunction with one or more MRBSs to provide a differential spectral interrogation or Q measurement. Such a differential measurement may eliminate all artifacts that may arise for example from bio-fouling (for in-vivo measurements). The emitted light spectral measurements may be performed with well known systems (not shown in the figures) that include an optical pumping mechanism (e.g. laser) and a remote optical reader (e.g. a spectrometer, a monochromator/detector combination, or a properly designed wavelength filter in conjunction with a detector), both coupled to the sensor(s) or combinations of sensor(s) and dummy(ies). MRBS arrays and measurements (both spectral interrogation of emitted light and Q measurements), in which more than one target substance is detected using arrays of sensors with different probes are also envisioned as within the scope of the present invention.

The sensors of the present invention have been described in detail with reference to a linear planar micro-resonator embodiment. It would be apparent to one skilled in the art that similar sensors may be made based on non-linear configurations including annular (e.g. as described by Scheuer et al), elliptical, multi-mirror type and other stable or unstable resonating structures. The sensors could be based either on resonators of passive type (i.e. changing the transmission or reflection spectral response as consequence of the sensing action) or of active type (including a PL material), allowing sensing by monitoring changes on the emission spectrum of the device. Advantageously, both the optical pumping and the optical monitoring may be done from the superstrate side.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A sensor comprising:
a) a substrate with a first refraction index;
b) a planar waveguide formed on the substrate and having a second refractive index larger than the first index, the waveguide including a light emitting material and at least one linear micro-resonator structure on a waveguide surface opposite to the substrate, the micro-resonator structure operative to output a light signal that includes a spectral response to an interaction between a target substance and the micro-resonator, the light being emitted upon optical pumping of the light emitting material.

2. The sensor of claim 1, wherein the micro-resonator includes a central section bound by two reflecting sections.

3. The sensor of claim 2, wherein each reflecting section includes a distributed Bragg reflector (DBR).

4. The sensor of claim 3, wherein the DBRs are identical.

5. The sensor of claim 3, wherein the DBRs include corrugations formed in the waveguide.

6. The sensor of claim 1, wherein the waveguide includes a sol-gel waveguide.

7. The sensor of claim 6, wherein the sol-gel is selected from the group consisting of $SiO_2$, $TiO_2$, $SiO_2/TiO_2$, $Ta_2O_3$ and a mixture thereof.

8. The sensor of claim 6, wherein the micro-resonator structure includes sections at least partially covered by a thin layer of a material different from the sol-gel.

9. The sensor of claim 8, wherein the material different from the sol-gel includes at least one metal.

10. The sensor of claim 9 wherein the at least one metal includes gold.

11. The sensor of claim 1, wherein the light emitting material includes a photoluminescent (PL) material.

12. The sensor of claim 1, wherein the micro-resonator structure includes two reflecting sections bounding a central section, the reflecting sections including periodic perturbations formed on the waveguide, and wherein the waveguide includes a sol-gel waveguide, the sensor further comprising:
c) at least one probe selected from the group consisting of at least one biological target binding material and at least one chemical target binding material, the probe fixated to at least a part of the micro-resonator structure.

13. The sensor of claim 12, wherein the periodic perturbations include a material selected from the group consisting of the probe and at least one metal.

14. A sensing device comprising:
a) at least one linear planar micro-resonator structure included in a light emitting waveguide that incorporates a light emitting material; and
b) at least one probe material bound to at least part of at least one micro-resonator structure, the probe material operative to bind specifically and selectively to a respective target substance, the specific and selective binding resulting in a parameter change in light emitted from the light emitting material upon optical pumping.

15. The sensing device of claim 14, wherein each linear planar micro-resonator structure includes a central region bound by two distributed Bragg reflectors (DBRs), the DBRs having corrugation tops and bottoms, the micro-resonator having at least one transverse mode.

16. The sensing device of claim 15, wherein the light emitting material includes a sol-gel material doped with a photoluminescent (PL) material, whereby the sensing device is active.

17. The sensing device of claim 16 wherein the parameter change includes a measurable quality factor (Q) change.

18. The sensing device of claim 16, wherein the parameter change includes a measurable spectral change.

19. The sensing device of claim 18, wherein the spectral change includes a wavelength shift.

20. The sensing device of claim 16, wherein the sol-gel is selected from the group consisting of $SiO_2$, $TiO_2$, $SiO_2/TiO_2$, $Ta_2O_3$ and a mixture thereof.

21. The sensing device of claim 16, further comprising at least one surface plasmon resonance (SPR) element coupled to the micro-resonator structure, wherein the parameter change includes a change in a resonant wavelength of the emitted light.

22. The sensing device of claim 15, wherein the parameter change includes a measurable quality factor (Q) change.

23. The sensing device of claim 15, wherein the waveguide includes a sol-gel is selected from the group consisting of $SiO_2$, $TiO_2$, $SiO_2/TiO_2$, $Ta_2O_3$ and a mixture thereof.

24. The sensing device of claim 15, wherein at least part of at least one micro-resonator structure includes a part selected from the group consisting of all the DBR corrugation tops, all the DBR corrugation bottoms, part of the corrugation tops and part of the corrugation bottoms.

25. The sensing device of claim 15, wherein the at least one transverse mode includes a plurality of N transverse modes, the device further comprising a plurality of longitudinal in-plane corrugations perpendicular to the DBR corrugations and operative to reduce the plurality to at least N−1.

26. The sensing device of claim 14, wherein the at least one probe material is selected from the group consisting of at least one biological target binding material and at least one chemical target binding material.

27. An optical sensing method for sensing remotely an interaction between a probe and a target substance, comprising the steps of:

a) providing at least one linear micro-resonator formed in a planar sol-gel waveguide that includes a light emitting material, at least one of the micro-resonators having at least one probe bound to at least a micro-resonator surface part;

b) promoting a specific and selective binding between the at least one probe and the target substance;

c) remotely optically pumping the waveguide, thereby causing a parameter change in light emitted therefrom though at least part of the micro-resonator; and d) remotely reading the parameter change.

28. The method of claim 27, wherein the step of reading the parameter change includes reading a spectral change.

29. The sensing device of claim 28, wherein the step of reading a spectral change includes reading a wavelength shift.

30. The method of claim 27, wherein the step of reading a parameter change includes reading a quality factor (Q) change.

31. The method of claim 30, wherein the step of reading a Q change includes reading a change selected from the group consisting of an emission spectral bandwidth change and an emission relaxation time change.

32. The method of claim 27, wherein the step of providing at least one linear planar micro-resonator includes providing at least two micro-resonators, at least one micro-resonator having at least one probe bound to at least a micro-resonator part and at least another micro-resonator being probe-free, and wherein the step of remotely reading the parameter change includes reading the parameter change differentially.

33. The method of claim 27, wherein the at least one probe is selected from the group consisting of at least one biological target binding material and at least one chemical target binding material.

* * * * *